(12) United States Patent
Gault et al.

(10) Patent No.: US 6,261,270 B1
(45) Date of Patent: Jul. 17, 2001

(54) SLEEVE STOPPER

(75) Inventors: Donald L. Gault, Wooster, OH (US); John F. Sergot, Antioch, IL (US); Max W. Shull, Ashland, OH (US); Gregory P. Talese, Wooster, OH (US); Richard A. Titus, Jr., Medina, OH (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/159,364

(22) Filed: Sep. 23, 1998

(51) Int. Cl.[7] ................................................... A61M 5/14
(52) U.S. Cl. ........................ 604/256; 604/246; 604/905; 604/415
(58) Field of Search ..................................... 604/244, 246, 604/256, 905, 415; 251/149.1; 215/355, 50, 296, 10; D09/439; 220/801, 350, 380; 383/96

(56) References Cited

U.S. PATENT DOCUMENTS

| | | | |
|---|---|---|---|
| 3,623,475 | * 11/1971 | Sanz et al. | 128/2 R |
| 3,900,028 | * 8/1975 | McPhee | 128/272 |
| 4,143,853 | * 3/1979 | Abramson | 251/149.1 |
| 4,187,893 | * 2/1980 | Bryan | 150/8 |
| 4,202,334 | * 5/1980 | Elson | 128/272 |
| 4,936,841 | * 6/1990 | Aoki et al. | 604/413 |
| 4,950,254 | * 8/1990 | Andersen et al. | 604/247 |
| 5,222,948 | * 6/1993 | Austin et al. | 604/213 |
| 5,267,983 | * 12/1993 | Oilschlager et al. | 604/283 |
| 5,395,351 | * 3/1995 | Munsch | 604/256 |
| 5,409,477 | * 4/1995 | Caron et al. | 604/407 |
| 5,425,465 | * 6/1995 | Healy | 215/355 |
| 5,540,674 | * 7/1996 | Karas et al. | 604/415 |
| 5,620,433 | * 4/1997 | Aswad et al. | 604/403 |
| 5,848,994 | * 12/1998 | Richmond | 604/248 |

* cited by examiner

Primary Examiner—Corrine McDermott
Assistant Examiner—Cris L. Rodriguez
(74) Attorney, Agent, or Firm—Brian R. Woodworth

(57) ABSTRACT

A sleeve stopper for use with a port. The sleeve stopper comprises a stopper body having a central membrane portion, a female portion and a male portion, the female and male portions extending from respective opposite sides of the membrane portion. A free end of the female portion defines an inside diameter which is less than an outside diameter defined at a free end of the male portion.

4 Claims, 2 Drawing Sheets

SLEEVE STOPPER

TECHNICAL FIELD

The present invention relates generally to sleeves used with containers and tubing sets, and more particularly to an improved sleeve stopper which is configured to preclude telescopic nesting of adjacent stoppers during the manufacture and handling thereof.

BACKGROUND OF THE INVENTION AND TECHNICAL PROBLEMS POSED BY THE PRIOR ART

Sleeve-like stoppers are widely used in association with tubing sets and containers used in the administration of intravenous solutions to patients. These types of stoppers ordinarily include a pierceable membrane portion and a side wall portion. The stopper is attached to a port on the tubing set, container, or other device such that the pierceable membrane sealingly covers the port. The side wall portion retains the pierceable membrane portion on the port. Fluids can be introduced into and/or withdrawn from the tubing set, container, or device by inserting a piercing member, e.g., a needle or a cannula, through the pierceable membrane, thereby providing fluid communication between the interior of the tubing set, container, or device and the exterior environment thereof.

In medical applications, sleeve stoppers of this type allow medical personnel to withdraw finite amounts of fluid from the tubing set or medical container without compromising the sterility of the fluid. It will be appreciated that standard medical cannulas, including, but not limited to, hypodermic syringes, can be used to pierce the pierceable membrane and provide the necessary fluid communication across the membrane. Such stoppers are particularly useful in connection with the addition of fluids into tubing sets and medical containers. For example, when used in connection with a Y-port on a medical tubing set, as depicted in FIG. 1, the sleeve stopper can be used to seal an "add port" on the Y-port device. A medical professional can introduce a secondary fluid into the tubing set for delivery to a patient by simply inserting a piercing member through the pierceable membrane and flowing a fluid into the tube set. Sleeve stoppers of this type also are useful to dilute medicaments or to facilitate the mixing of two or more fluids in containers of known construction.

A heretofore known sleeve stopper of the above-discussed type has a generally stepped, cylindrical configuration, including male and female portions. The male portion is configured to be received within a tubular port of a tubing set or a container, while the female portion, in turn, is of a relatively larger size and is configured to receive therein a wall defining tubular port. In this way, the sleeve stopper can be used to fluidly seal a port associated with the tubing set or container. In such an arrangement, the male portion has an outside diameter at its free end which is less than the inside diameter of the end of the female portion when the sleeve stopper is in its first position, that is, the position reflected in FIG. 2.

By virtue of this relative dimensioning, a problem can occur attendant to manufacture and handling of adjacent sleeve stoppers. In particular, undesired "snaking" of the stoppers can occur when the male portion of one stopper telescopically nests within the female portion of an adjacent stopper. This effect can create an elongated "snake" of stopper parts, and can detract from efficient operation of automatic handling equipment.

SUMMARY OF THE INVENTION

The present invention is directed to a sleeve stopper which has been particularly configured to avoid the problem of "snaking" heretofore exhibited during the automatic handling of previously known sleeve stoppers. In particular, the present sleeve stopper is configured such that a male portion of the stopper is dimensioned so that it cannot be readily received within the female portion of an adjacent stopper. This arrangement significantly reduces the possibility of the nesting or snaking of adjacent sleeve stoppers, thereby promoting efficient/economical handling with automated equipment.

In accordance with the illustrated embodiment, the present sleeve stopper comprises a stopper body having a central membrane portion constructed of a pierceable material. In one embodiment, the pierceable material is selected such that it reseals itself upon the withdrawal of a piercing member therefrom. The stopper body further includes a female portion extending from one side of the membrane portion. The body also includes a male portion which extends from an opposite side of the membrane portion. The female portion is constructed such that it substantially surrounds an exterior wall of the male portion when the stopper body is in use, i.e., when the stopper body is in its second position.

In one embodiment, each of the male and female portions comprises a respective annular wall defining an interior passage. The passages are separated and fluidly sealed from one another by the membrane portion, with the passages being fluidly connected when a piercing member, e.g., a needle or a cannula, pierces the membrane portion. In accordance with the present invention, the annular wall of the female portion defines an inside diameter $D_1$ at a free end thereof when the stopper body is in its first position, while the annular wall of the second, male portion defines an outside diameter $D_2$ at the free end portion thereof. The outside diameter $D_2$ of the male portion is greater than the diameter $D_1$ of the female portion to thereby preclude telescopic nesting of adjacent sleeve stoppers. This promotes efficient handling with automated equipment.

In the illustrated embodiment, the membrane portion includes an annular indicia or target positioned adjacent to the passage defined by the annular wall of the female sleeve portion. This target facilitates connection of associated components by directing a user to the appropriate location for piercing the membrane portion.

An annular wall of the female portion defines a relatively thick, annular bead on the free end portion thereof, with the annular bead defining the diameter $D_1$. To promote efficient manufacture, the walls of male and female portions preferably are tapered. Specifically, the annular wall of the female portion tapers inwardly in a direction toward the membrane portion when the body portion is in the first position, while the annular wall of the male portion tapers inwardly in a direction away from the membrane portion.

Other features and advantages of the present invention will become readily apparent from the following detailed description, the accompanying drawings, and the appended claims.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

Figure 1:
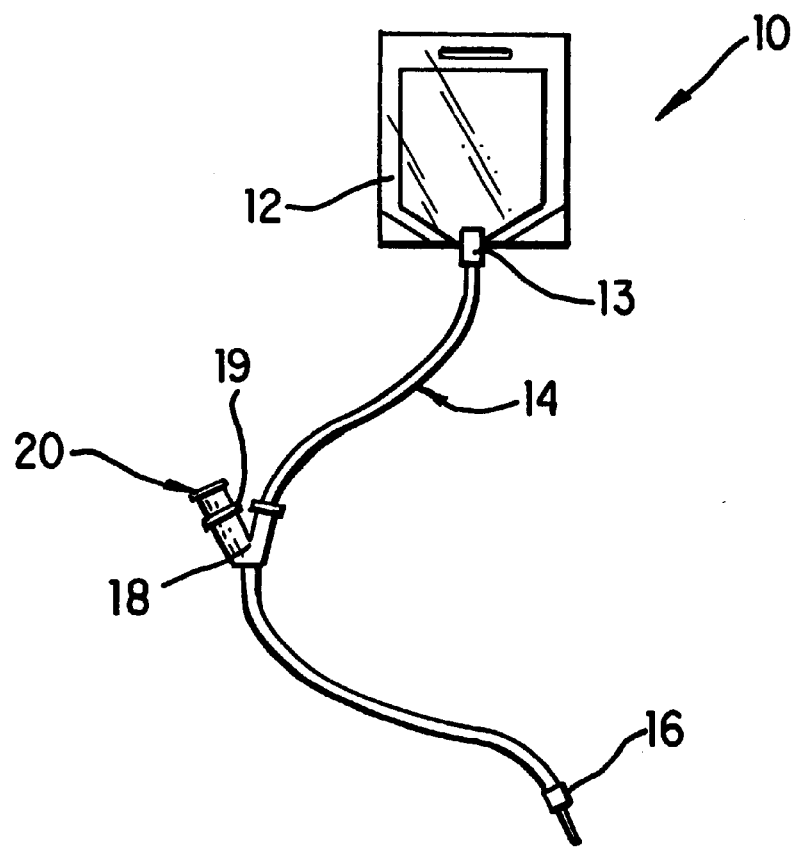
FIG. 1 is a diagrammatic view of a container and associated tubing set, the tubing set having a sleeve stopper mounted thereon.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

With reference to FIG. 1, therein is illustrated a solution administration set 10 of the type employed for administration of parenteral or enteral solutions to patients. The set 10 includes a container 12 constructed to contain a fluid. Container 12 can have a variety of known configurations, including known flexible and rigid containers. Container 12 depicted in FIG. 1 is a flexible container of a known construction typically used to contain parenteral or enteral liquid products. Container 12 includes a port 13 constructed to facilitate the introduction of fluid into and/or the withdrawal of fluid from container 12. Port 13 is also of a known construction and is substantially annular in cross-section.

In the embodiment of the present invention depicted in FIG. 1, tubing set 14 is mounted on port 13 such that an interior of tubing set 14 is in fluid communication with fluid within container 12. The connection between tubing set 14 and port 13 can be provided using a variety of known techniques including, but not limited to, luer, locking luer, and spike connections. As depicted in FIG. 1, tubing set 14 includes a cannula 16 or other stopper for administration of fluid to a patient. The tubing set 14 in the depicted embodiment further includes a Y-site 18, which defines an add port 19. Add port 19 facilitates the introduction of fluids into and/or the withdrawal of fluids from tubing set 14 without the need to open tubing set 14 to an external environment thereof. Add port 19 is of a known construction and is substantially annular in cross-section.

Sleeve stopper 20 constructed in accordance with the present invention is mounted on add port 19 in the embodiment depicted in FIG. 1. However, it is to be understood that sleeve stopper 20 can be used on a variety of other ports, including, but not limited to, port 13 on container 12, without departing from the spirit and scope of the present invention. The use of sleeve stopper 20 depicted in the accompanying figures is intended to be exemplary in nature and is not intended to limit the applications of sleeve stopper 20 of the present invention.

Figure 2:
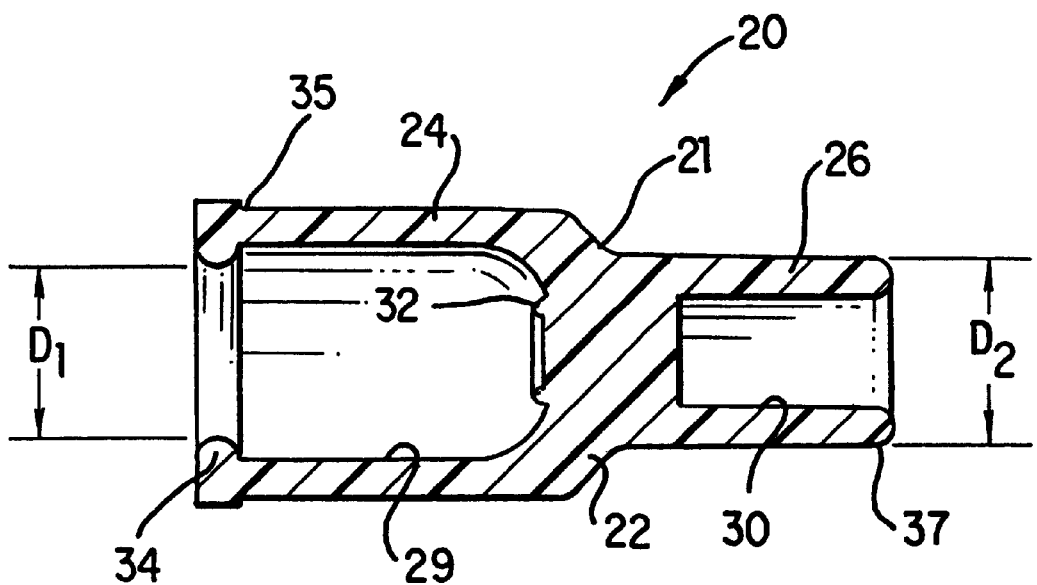
FIG. 2 is a cross-sectional view of a sleeve stopper of the present invention in a first position.

Sleeve stopper 20 has a body portion 21. As depicted in FIG. 2, body portion 21 is a unitary (i.e., one-piece) body having a central membrane portion 22, a female portion 24, and a male portion 26. However, it is to be appreciated that body 21 can be constructed of two or more pieces without departing from the spirit and scope of the present invention as defined by the appended claims. Membrane portion 22 is constructed to be pierceable by a piercing member such as a needle or cannula of known construction (not shown), whereby flow through the membrane portion 22 can be effected. The membrane portion 22 can be constructed of a variety of known materials used to seal fluid ports. In a preferred embodiment of the present invention, central membrane portion 22 is constructed of a known material that allows central membrane portion 22 to reseal itself when the piercing member is withdrawn from the membrane portion 22, thereby fluidly sealing the port on which sleeve stopper 20 is used after the piercing member is withdrawn.

The sleeve stopper 20 includes a first, female portion 24 extending from one side of the central membrane portion 22. The female portion 24 preferably is in the form of an annular wall defining an interior passage 28.

The sleeve stopper 20 further includes a second, male portion 26 extending from a second, opposite side of the central membrane portion 22. Male portion 26 is constructed for placement within a port, e.g., port 13 or port 19. In the embodiment of the present invention depicted in the accompanying figures, male portion 26 includes an annular wall, and defines an interior passage 30. In the depicted embodiment, piercing of the membrane portion 22 acts to permit flow generally through membrane portion 22 and through passage 30 of second, male portion 26. It will be appreciated that male portion 26 also can be constructed in the form of a plug rather than as an annular wall, that is, such that no interior passage 30 is defined by male portion 26. However, it is preferred that interior passage 30 be present in order to minimize the length of the piercing member that is required to pierce membrane portion 22. It will be appreciated that the dimensions and configuration of interior passage 30 can be varied without departing from the scope of the present invention.

An annular target 32 on the membrane portion 22 adjacent passage 28 facilitates penetration of the membrane portion 22. Annular target 32 can be in the form of a raised or depressed circular indicia on the surface of membrane portion 22. Alternatively, annular target 32 can be created by applying a contrasting color or pattern to a target surface of membrane portion 22.

In the embodiment of the present invention depicted in FIG. 2, the inside diameter of first, female portion 24 is generally equal to the outside diameter of the second, male sleeve portion 26. Heretofore, as above-discussed, this relative dimensioning of the components has led to undesired telescopic nesting of adjacent ones of the stoppers during processing, sometimes referred to as "snaking". This can interfere with efficient operation of automated handling equipment for the stoppers.

In accordance with the present invention, the dimensioning of the sleeve portions of the stopper has been specifically selected to preclude such telescopic nesting of a plurality of the stoppers during handling. In particular, the first sleeve portion 24 includes a relatively thick annular bead 34 at the free end portion 35 thereof, which annular bead 34 defines an inside diameter $D_1$. At the opposite free end portion 37 of stopper 20, free end portion 37 of male portion 26 defines an outside diameter $D_2$. The stopper is specifically configured such that $D_2$ is greater than $D_1$. As such, the second, male portion 26 is substantially precluded from becoming positioned within the first, female portion 24 of an adjacent stopper during handling. Telescopic nesting of a plurality of the stoppers is thus substantially avoided.

To facilitate molding of the stopper, the walls of each of the male and female portions 24, 26 are preferably tapered. In particular, the annular wall of the first, female portion 24 tapers inwardly in a direction toward the membrane portion 22. The annular wall of male portion 26 tapers inwardly in a direction away from the membrane portion 22.

The sleeve stopper 20 is preferably formed from suitable elastomeric materials. In a current embodiment, the unitary stopper body is constructed from a material that contains a natural rubber and/or a synthetic rubber, e.g., polyisoprene.

In a current embodiment, wherein the stopper body is approximately 0.63 inches in length, the annular bead 34 is configured to define an inside diameter $D_1$ of 0.162 inches, while the second sleeve portion 26 defines an outside diameter $D_2$ at the free end thereof of 0.171 inches.

Figure 3:
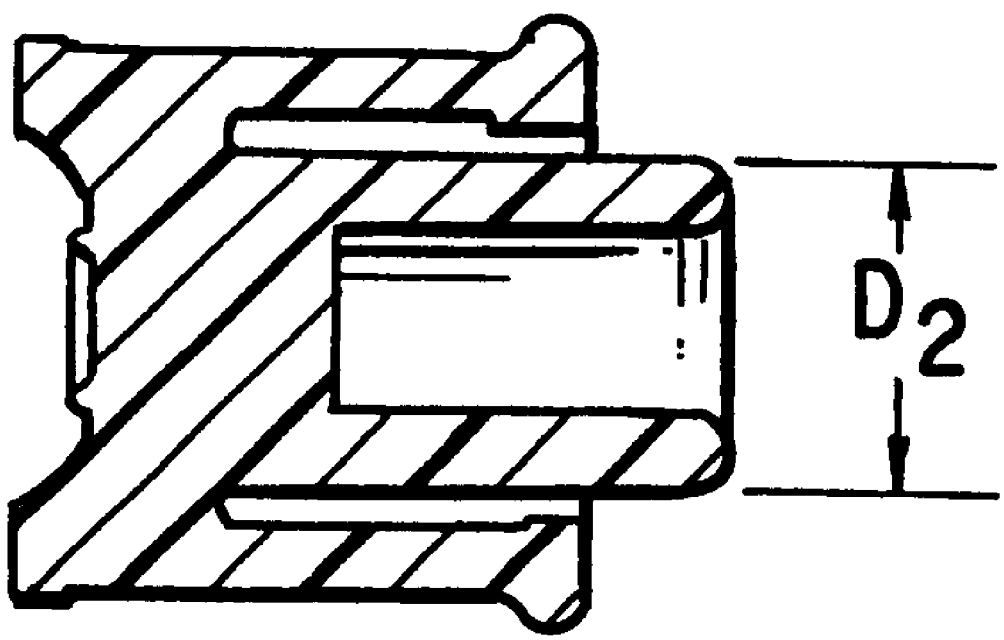
FIG. 3 is a cross-sectional view of a sleeve stopper of the present invention in a second position.

When in use with a port, e.g., port 13 or port 19, female portion 24 is inverted such that is in a second position depicted in FIG. 3. In the second position, a recess 39 defined between male portion 26 and female portion 24. Recess 39 is configured and dimensioned such that it receives an annular wall of a port therein such that sleeve stopper 20 is retained on the port. When sleeve stopper 20 is in its second position, annular bead 34 faces outwardly without interfering with the operation or efficacy of sleeve stopper 20.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover, by the appended claims, all such modifications as fall within the scope of the claims.

What is claimed is:

1. A sleeve stopper comprising:

a stopper body having a central membrane portion having a first side and a second side opposite said first side, a male portion extending from said first side of said membrane portion, and a female portion extending from said second side of said membrane portion, said male portion having an exterior wall constructed to be received within a port, said female portion comprising an annular wall defining an interior passage when said stopper body is in a first position, said annular wall having a surface facing said interior passage defined by said annular wall when said stopper body is in said first position, said annular wall having a free end portion spaced from said central membrane, said surface defining an inside diameter at said free end portion of said annular wall, said exterior wall of said male portion having a free end portion spaced from said central membrane, said exterior wall defining an outside diameter at said free end portion thereof, said outside diameter being greater than said inside diameter, said female portion constructed to be moved to a second position in which said annular wall is radially outwardly spaced from said male portion and in which said surface facing said interior passage defined by said annular wall when said stopper body is in said first position faces radially outwardly.

2. A sleeve stopper in accordance with claim 1, wherein said stopper body is constructed from a material comprising isoprene.

3. A closed container, said closed container comprising:

a container constructed to contain a fluid therein, said container defining a port, said port providing fluid communication between an interior of said container and an exterior environment of said container; and a sleeve stopper mounted on and fluidly sealing said port, said sleeve stopper comprising a stopper body having a central membrane portion having a first side and a second side opposite said first side, a male portion extending from said first side of said membrane portion, and a female portion extending from said second side of said membrane portion, said male portion having an exterior wall constructed to be received within said port, said female portion comprising an annular wall defining an interior passage when said stopper body is in a first position, said annular wall having a free end portion spaced from said central membrane, said annular wall having a surface facing said interior passage defined by said annular wall when said stopper body is in said first position, said surface defining an inside diameter at said free end portion of said annular wall, said exterior wall of said male portion having a free end portion spaced from said central membrane, said exterior wall defining an outside diameter at said free end portion thereof, said outside diameter being greater than said inside diameter, said female portion constructed to be moved to a second position in which said annular wall is radially outwardly spaced from said male portion and in which said surface facing said interior passage defined by said annular wall when said stopper body is in said first position faces radially outwardly.

4. A tubing set for delivering fluid from a fluid source to a patient, said tubing set comprising:

length of tubing having a first end portion and a second end portion, said first end portion constructed for fluid connection to a fluid source, said second end portion constructed for fluid connection to an apparatus for delivery of a fluid to a patient, said length of tubing a defining a port therein intermediate said first and second end portions, said port providing fluid communication between an interior environment of said tubing set and an exterior environment of said tubing set; and a sleeve stopper mounted on and fluidly sealing said port, said sleeve stopper comprising a stopper body having a central membrane portion having a first side and a second side opposite said first side, a male portion extending from said first side of said membrane portion, and a female portion extending from said second side of said membrane portion, said male portion having an exterior wall constructed to be received within said port, said female portion comprising an annular wall defining an interior passage when said stopper body is in a first position, said annular wall having a surface facing said interior passage defined by said annular wall when said stopper body is in said first position, said annular wall having a free end portion spaced from said central membrane, said surface defining an inside diameter at said free end portion of said annular wall, said exterior wall of said male portion having a free end portion spaced from said central membrane, said exterior wall defining an outside diameter at said free end portion thereof, said outside diameter being greater than said inside diameter, said female portion constructed to be moved to a second position in which said annular wall is radially outwardly spaced from said male portion and in which said surface facing said interior passage defined by said annular wall when said stopper body is in said fist position faces radially outwardly.

* * * * *